(12) United States Patent  
Watanabe (10) Patent No.: US 7,924,982 B2
(45) Date of Patent: Apr. 12, 2011

(54) RADIOGRAPHIC IMAGING APPARATUS AND CONTROL METHOD THEREOF

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 79 days.

(21) Appl. No.: 12/506,360

(22) Filed: Jul. 21, 2009

(65) Prior Publication Data

US 2010/0054404 A1    Mar. 4, 2010

(30) Foreign Application Priority Data

Aug. 28, 2008    (JP) ................................ 2008-220500

(51) Int. Cl.
*H05G 1/56* (2006.01)
(52) U.S. Cl. .......................... 378/114; 378/62; 378/116
(58) Field of Classification Search .................... 378/62, 378/98.8, 114–116; 250/370.08, 370.09
See application file for complete search history.

(56) References Cited

U.S. PATENT DOCUMENTS
2009/0154648 A1    6/2009    Watanabe ..................... 378/116

FOREIGN PATENT DOCUMENTS
JP    2005-000470    1/2006

*Primary Examiner* — Courtney Thomas
(74) *Attorney, Agent, or Firm* — Fitzpatrick, Cella, Harper & Scinto (57) ABSTRACT

A radiographic imaging apparatus includes a radiation generator which irradiates an object with radiation, a detection unit which detects the radiation generated by the radiation generator and transmitted through the object, thereby shooting a radiographic image, and a control unit which controls radiographic imaging by the radiation generator and the detection unit. The detection unit includes a first connection unit to be used to connect the control unit when used portably, and a second connection unit to be used to connect the control unit when stationarily used on a support portion. The detection unit detects which one of the first connection unit and the second connection unit is used to connect the control unit, and determines a shooting operation based on the detection result.

7 Claims, 10 Drawing Sheets

RADIOGRAPHIC IMAGING APPARATUS AND CONTROL METHOD THEREOF

BACKGROUND OF THE INVENTION

1. Field of the Invention

The present invention relates to a radiographic imaging apparatus for radiographically imaging an object using radiation and a control method thereof.

2. Description of the Related Art

There is an apparatus conventionally known which irradiates a target object with radiation and detects the intensity distribution of radiation transmitted through the target object, thereby obtaining a radiographic image of the target object. Such an apparatus is widely used in industrial nondestructive inspection and medical diagnosis.

The shooting is commonly conducted by a film/screen method using radiation. This method enables shooting by combining a photosensitive film and a phosphor sensitive to radiation. In this method, sheets of a rare-earth phosphor that emit light when irradiated with radiation are held in tight contact with both sides of a photosensitive film. The phosphor converts radiation transmitted through an object into visible light. The photosensitive film captures the light. A latent image formed on the film is then developed into a visible image by chemical treatments.

Recent progress of digital technologies has popularized a scheme of converting a radiographic image into an electrical signal, processing the electrical signal, and reproducing it as a visible image on a CRT or the like, thereby obtaining a high-quality radiographic image. To convert a radiographic image into an electrical signal, a radiographic image recording/reproduction system has been proposed. This system temporarily accumulates an image of transmitted radiation in a phosphor as a latent image. The latent image is then photoelectrically read out by irradiating it with excitation light such as a laser beam and output as a visible image.

An apparatus for shooting a radiographic image using a semiconductor sensor has also been known along with recent advance in semiconductor process technologies. This system has a dynamic range much wider than that of a conventional radiographic system using photosensitive films and can obtain a radiographic image without being affected by variations in the exposure amount of radiation. The system can also immediately obtain an output image because no chemical treatment is necessary, unlike the conventional scheme using photosensitive films.

Figure 12:
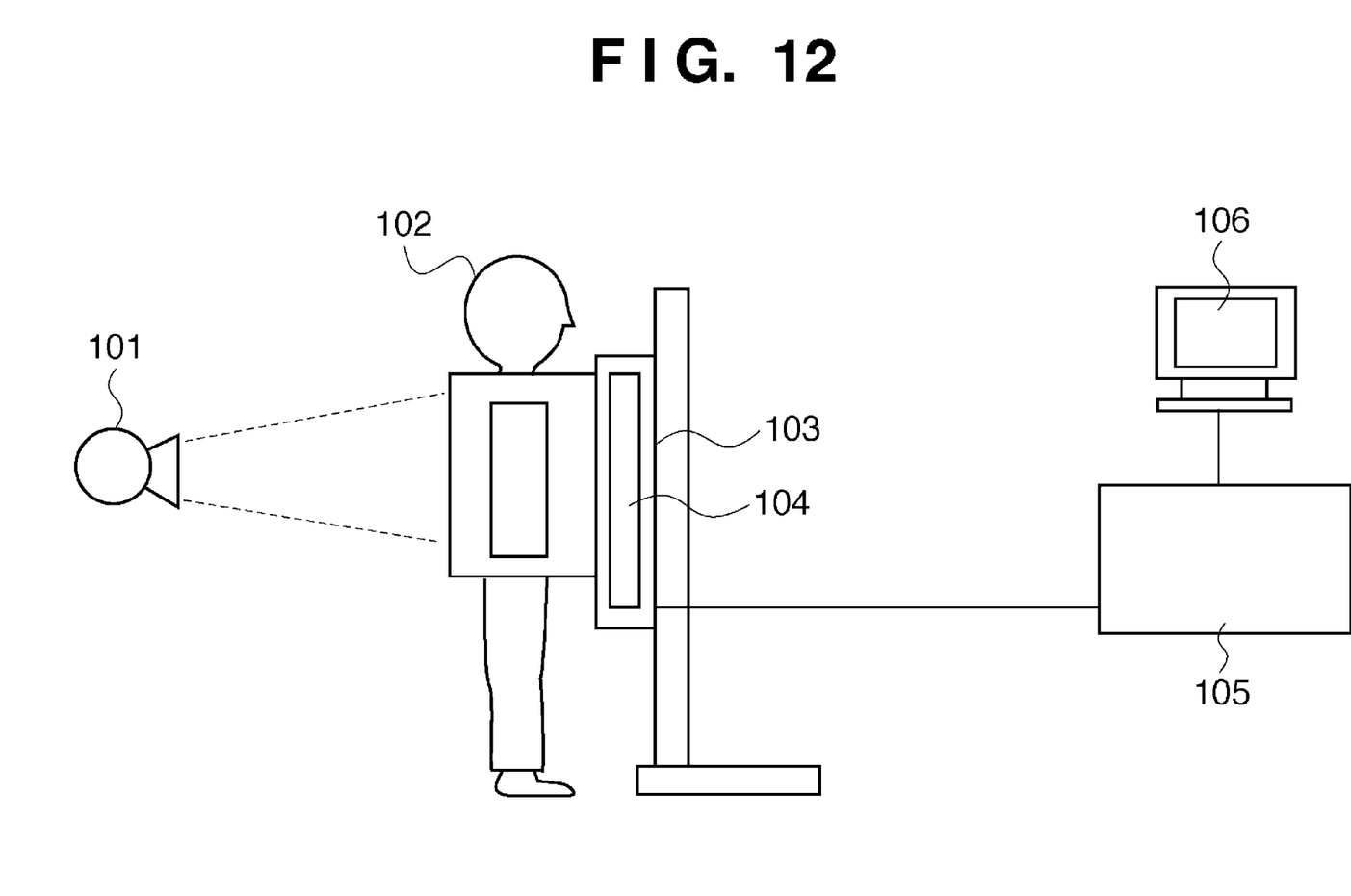
FIG. 12 is a view for explaining a conventional technique.

FIG. 12 is a schematic view showing a system using such a radiographic imaging apparatus.

A radiographic imaging apparatus 103 (to be abbreviated as an X-ray imaging unit hereinafter) incorporates a radiation detection sensor 104. Radiation emitted by a radiation generator 101 irradiates an object 102. The radiation transmitted through the object is converted into visible light via a phosphor and detected as an electrical signal by photoelectric conversion elements arrayed in a two-dimensional matrix. The system includes a control unit 105 which controls read drive of the radiation detection sensor 104 and image transfer. Under the control of the control unit 105, an image output from the X-ray imaging unit 103 undergoes digital image processing so that a monitor 106 displays a radiographic image of the object.

This system can advantageously monitor an image immediately, unlike the above-described radiographic image recording/reproduction system. In this system, the X-ray imaging unit is generally installed in a dedicated frame stationarily placed in a radiographic examination room to shoot an object in, as examples, a standing or lying position. Portable X-ray imaging units which have been developed in recent years also enable shooting at an arbitrary shooting posture. Japanese Patent Laid-Open No. 2005-000470 proposes a technique of stationarily supporting a portable X-ray imaging unit at a position opposing a tube and a technique of independently using it separated from the support portion. The former technique facilitates positioning so as to quickly perform accurate alignment. The latter technique that allows to place the X-ray imaging unit at an arbitrary position is applicable to an immovable object to reduce his/her burden. According to the techniques proposed in Japanese Patent Laid-Open No. 2005-000470, it is possible to implement two shooting forms by one apparatus and therefore improve the convenience.

However, when implementing the two different shooting forms by a single apparatus, there is also a problem to solve to optimize the apparatus for each form.

The medical field tends to be backward in prompting wireless communication for fear of interference between apparatuses, influence on pacemakers, and reliability of wireless communication. In fact, the above-described X-ray imaging unit also uses cables to supply power to the apparatus and transmit/receive information. When shooting the radiographic image using the X-ray imaging unit incorporated in a cassette, a human body gets on the apparatus in many cases. Hence, the cables which are led from a side surface not to make unevenness in the direction of thickness have a flexible structure in consideration of leading operability. On the other hand, when the X-ray imaging unit is supported in a frame, there is a high possibility that cable leading to a side surface of the apparatus impedes human body alignment and operations. In this case, the communication speed has priority over the flexibility of cables in the specifications.

SUMMARY OF THE INVENTION

The present invention provides a radiographic imaging apparatus capable of realizing both convenience when portably using a detector and high performance when stationarily using the detector and a control method thereof.

According to a first aspect of the present invention, there is provided a radiographic imaging apparatus comprising: a radiation generator configured to irradiate an object with radiation; a detection unit configured to detect the radiation generated by the radiation generator and transmitted through the object, thereby shooting a radiographic image; and a control unit configured to control radiographic imaging by the radiation generator and the detection unit, the detection unit comprising: a first connection unit configured to be used to connect the control unit when used portably; a second connection unit configured to be used to connect the control unit when stationarily used on a support portion; a connection destination detection unit configured to detect which one of the first connection unit and the second connection unit is used to connect the control unit; and a determination unit configured to determine a shooting operation based on a detection result of the connection destination detection unit, wherein upon detecting connection by the first connection unit, the determination unit makes a frame rate of shooting lower than that in connection by the second connection unit.

According to a second aspect of the present invention, there is provided a control method of a radiographic imaging apparatus including: a radiation generator configured to irradiate an object with radiation; a detection unit configured to detect the radiation generated by the radiation generator and transmitted through the object, thereby shooting a radiographic image; and a control unit configured to control radiographic imaging by the radiation generator and the detection unit, the method comprising: detecting which one of a first connection unit provided in the detection unit and used to connect the control unit when portably using the detection unit and a second connection unit provided in the detection unit and used to connect the control unit when stationarily using the detection unit on a support portion is used to connect the detection unit to the control unit; and determining a shooting operation based on a detection result in the detecting which one of the first connection unit and the second connection unit is used to connect the detection unit to the control unit, wherein upon detecting connection by the first connection unit, a frame rate of shooting is made lower than that in connection by the second connection unit in the determining of the shooting operation.

Further features of the present invention will become apparent from the following description of exemplary embodiments (with reference to the attached drawings).

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
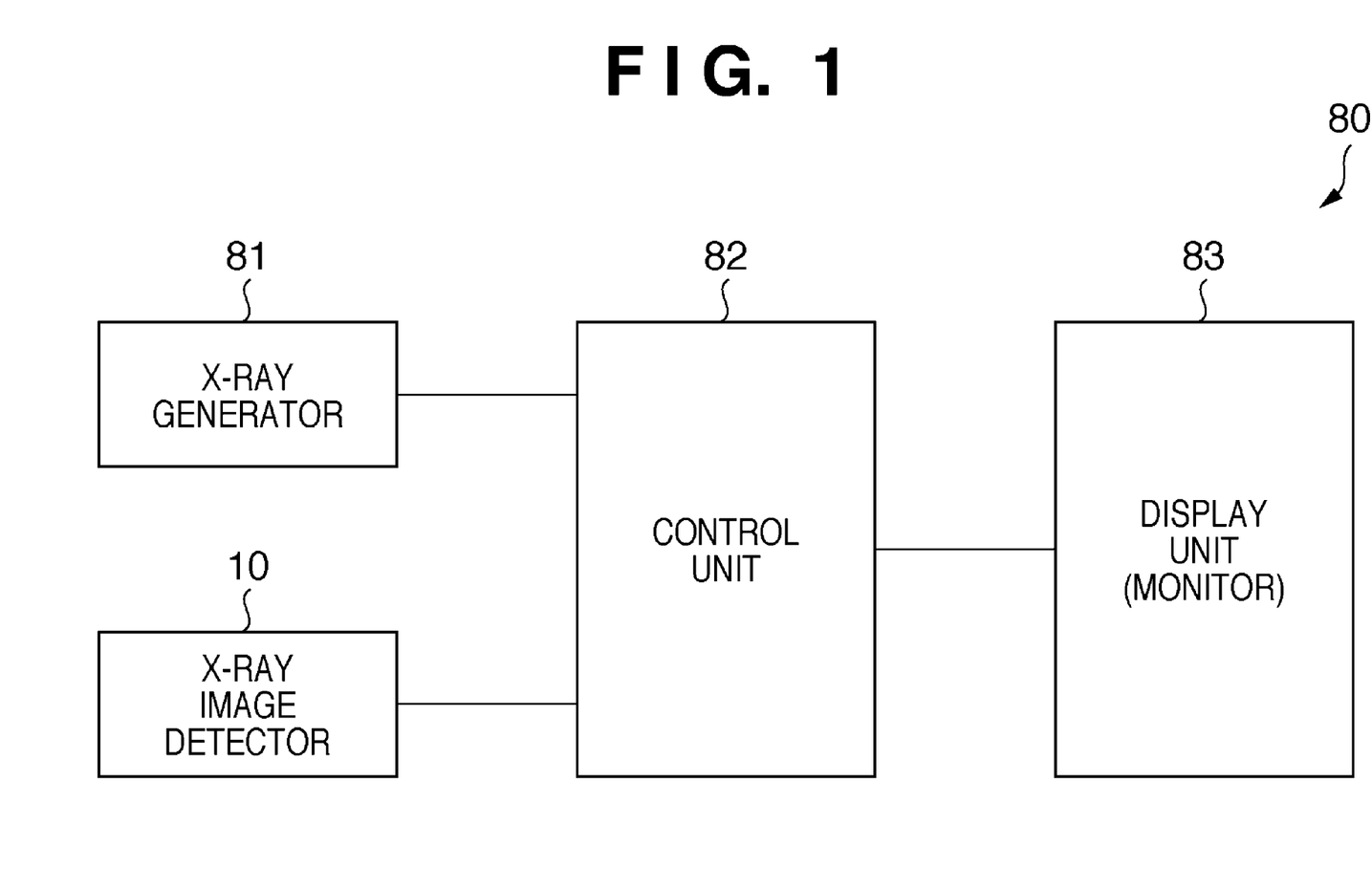
FIG. 1 is a block diagram showing an example of the functional arrangement of a radiographic imaging apparatus (to be abbreviated as an X-ray imaging apparatus) according to an embodiment of the present invention.

FIG. 1 is a block diagram showing an example of the functional arrangement of a radiographic imaging apparatus (to be abbreviated as an X-ray imaging apparatus hereinafter) according to an embodiment of the present invention.

An X-ray imaging apparatus 80 includes one or a plurality of computers. The computer includes a main control unit such as a CPU and storage units such as a ROM (Read Only Memory) and a RAM (Random Access Memory). The computer may also include a communication unit such as a network card and input/output units such as a keyboard and a display or touch panel. These constituent elements are connected by a bus and the like and controlled by causing the main control unit to execute programs stored in the storage units.

The X-ray imaging apparatus 80 includes an X-ray generator 81, an X-ray image detector 10, a control unit 82, and a display unit (monitor) 83.

The X-ray generator (i.e., radiation generator) 81 emits radiation (X-rays) toward an object (e.g., human body). The X-ray image detector 10 shoots an X-ray image based on the object by detecting the radiation emitted by the X-ray generator 81 and transmitted through the object. The control unit 82 collectively controls processing of the X-ray imaging apparatus 80. For example, the control unit 82 controls radiographic imaging (X-ray imaging) by the X-ray generator 81 and the X-ray image detector 10. The control unit 82 also controls read drive of the X-ray image detector 10 and image transfer. The display unit 83 displays the X-ray image of the object shot by the X-ray image detector 10.

An example of the functional arrangement of the X-ray imaging apparatus 80 has been described above. However, the functional arrangement provided in the apparatus need not always be implemented as illustrated. For example, the above-described functional arrangement may be provided in each of a plurality of apparatuses to implement a system.

Figure 2:
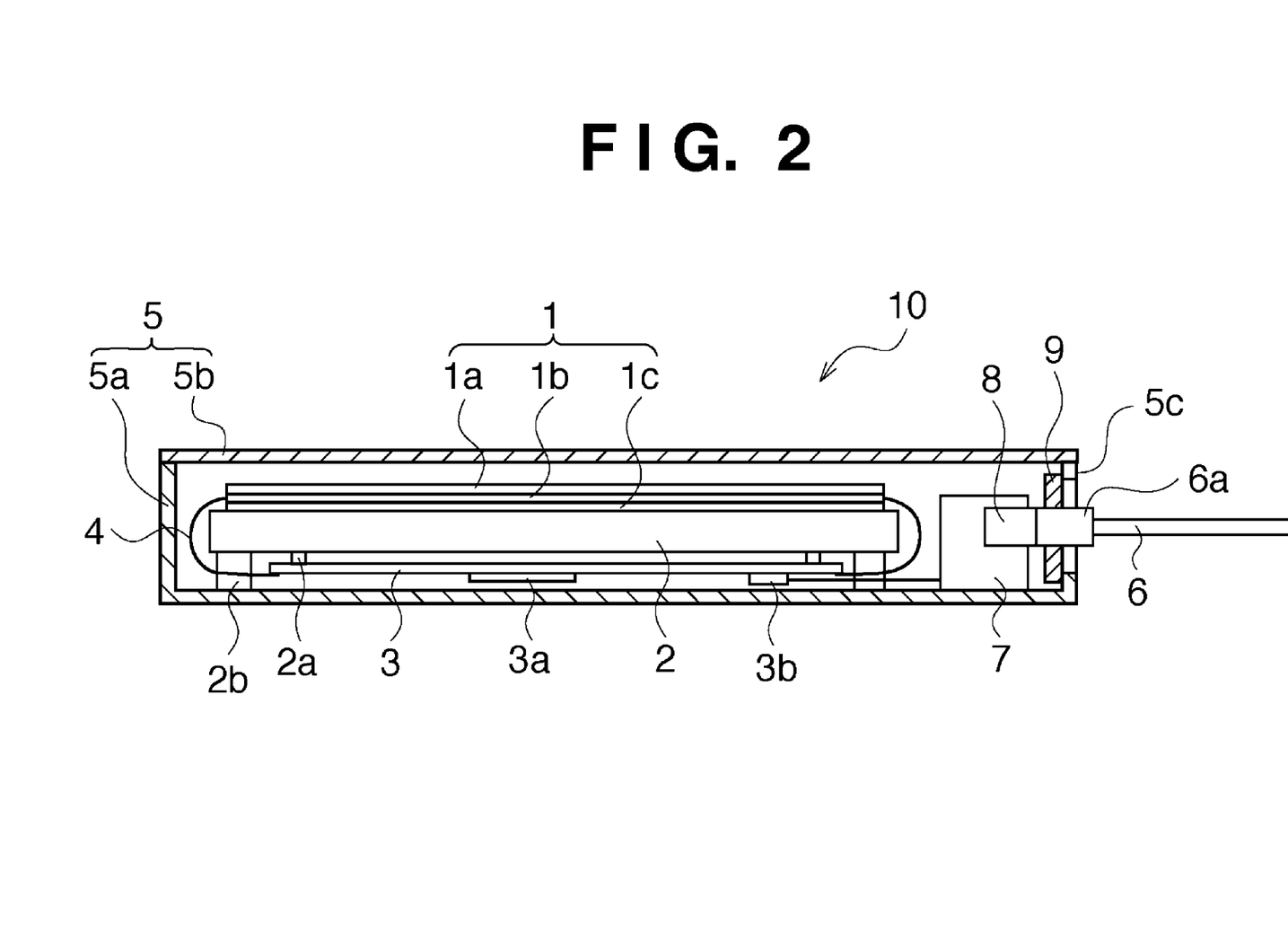
FIG. 2 is a sectional view showing an example of the internal section of an X-ray image detector 10 shown in FIG. 1.
Figure 3:
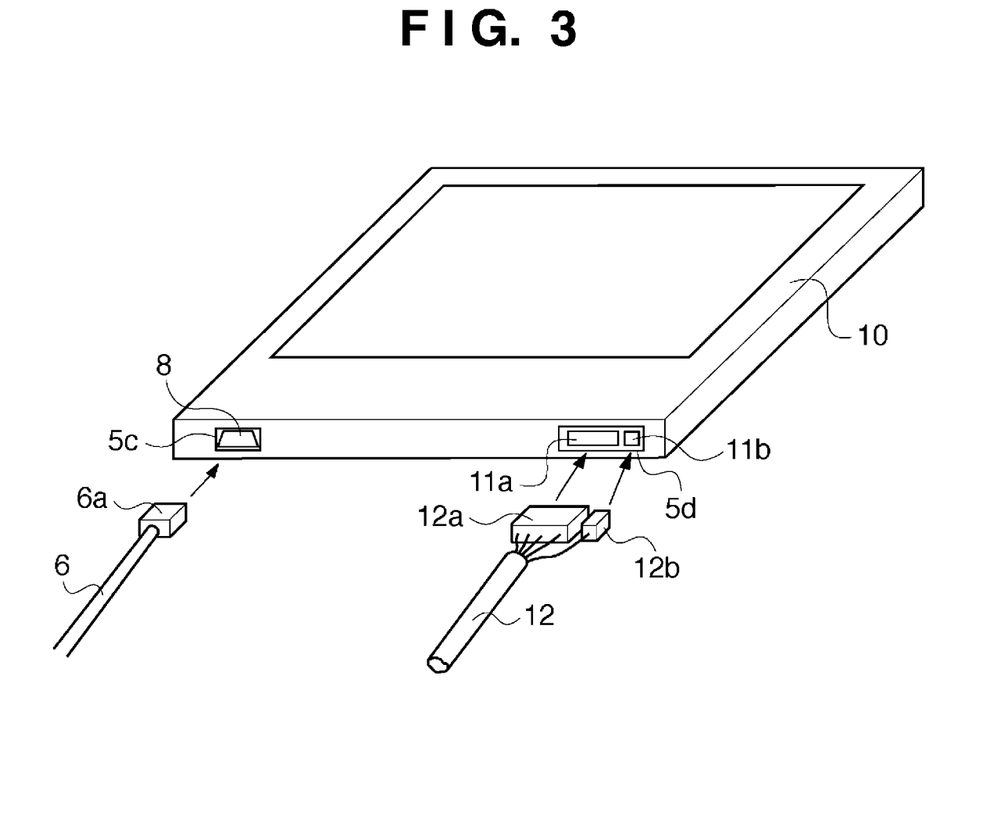
FIG. 3 is a perspective view showing an example of the outer appearance of the X-ray image detector 10 shown in FIG. 1.
Figure 4:
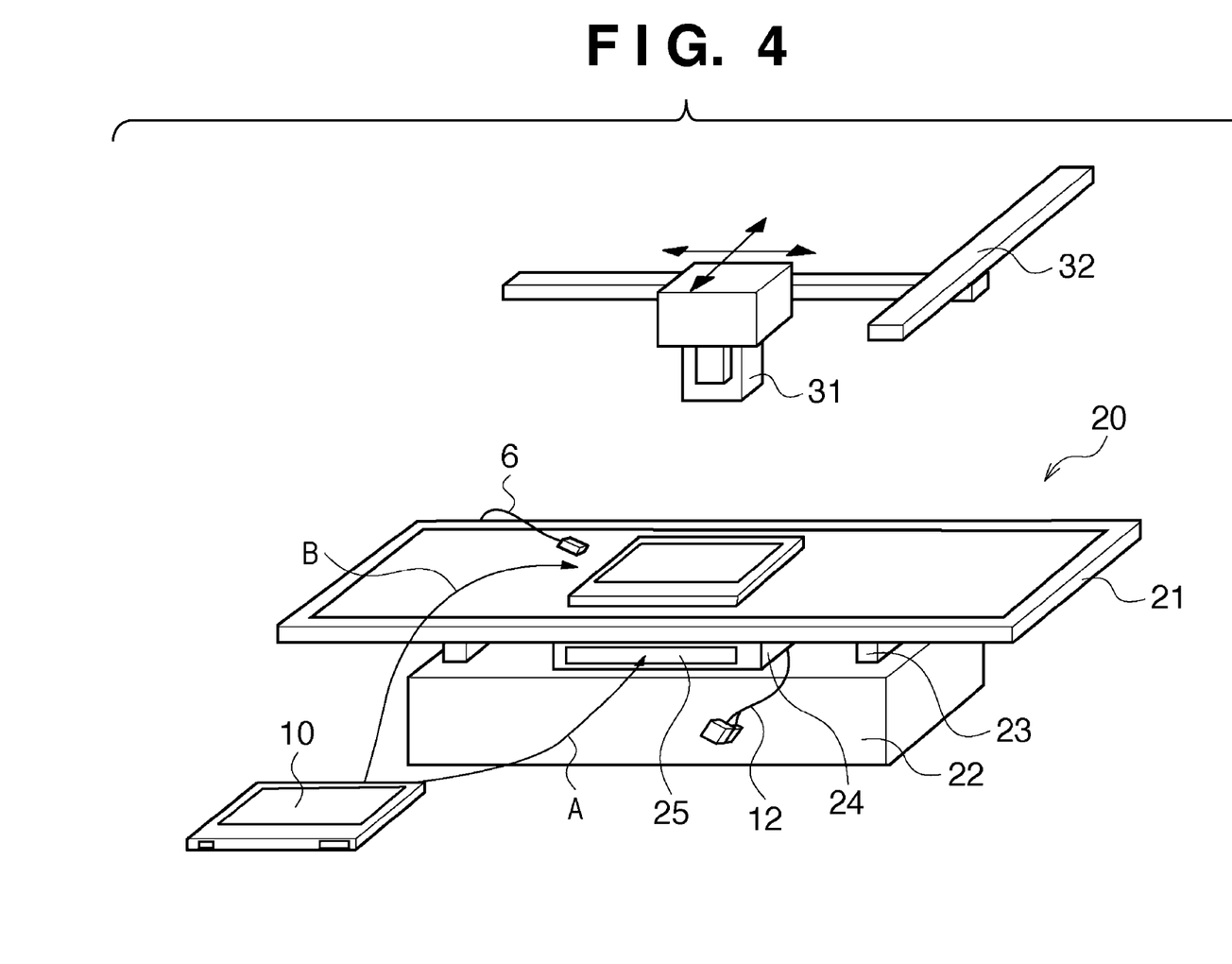
FIG. 4 is a perspective view showing an example in which the X-ray image detector 10 shown in FIG. 1 is attached to a support portion for detachably supporting it.

The X-ray image detector shown in FIG. 1 will be described next with reference to FIGS. 2 to 4. FIG. 2 is a sectional view showing an example of the internal section of the X-ray image detector 10. FIG. 3 is a perspective view showing an example of the outer appearance of the X-ray image detector 10. FIG. 4 is a perspective view showing an example in which the X-ray image detector 10 is attached to a support portion for detachably supporting it.

Referring to FIG. 2, an X-ray image detection panel 1 fundamentally includes a fluorescent screen 1a, photoelectric conversion elements 1b, and a substrate 1c. As the substrate 1c, a glass plate is often used because it needs to avoid any chemical actions with the semiconductor element, stand the temperatures of semiconductor processes, and have dimensional stability. The photoelectric conversion elements 1b are formed two-dimensionally on the glass substrate by the semiconductor processes. The fluorescent screen 1a is made by applying a phosphor of a metal compound to a resin plate and integrated with the substrate 1c by bonding. These elements which form the X-ray image detection panel 1 are fixed on a metal base 2.

A circuit board 3 which processes an electrical signal obtained by photoelectric conversion is connected to the photoelectric conversion elements 1b via a flexible circuit board 4 and fixed on the back side of the base 2. The base 2 is fixed in a case main body 5a and hermetically sealed by a case cover 5b made of a material having a high X-ray transmittance, thereby constituting the X-ray image detector 10 of the X-ray imaging apparatus 80. X-ray imaging is enabled by combining the X-ray image detector 10 with a tube for emitting X-rays.

When X-rays transmitted through the object become incident on the X-ray image detector 10 from the upper side in FIG. 2, the fluorescent screen 1a emits light. The two-dimensionally arrayed photoelectric conversion elements 1*b* convert the light into an electrical signal. A digital image is thus obtained. The digital image is transferred to the control unit 82 via an external communication unit 7. This allows the user to view the shot image immediately on the monitor.

Charges are read from the X-ray image detection panel 1 by removing charges accumulated in the plurality of photoelectric conversion elements 1*b* of a column selected by a driving circuit in the row direction and making a reading circuit unit arranged in correspondence with each row read the charges. When driving the X-ray image detector 10, the electronic components 3 and 4 generate heat as they consume power. The heat generated by the electronic components increases the temperature inside the X-ray image detector 10 and is dissipated via a case 5. The X-ray image detector 10 needs to have a power supply unit and a signal transfer unit for power supply and signal transfer during image reading. In this embodiment, the X-ray image detector 10 is connected to the external control unit 82. Hence, the X-ray image detector 10 has two openings 5*c* and 5*d* on a side surface, i.e., a surface perpendicular to the radiation incident surface, as shown in FIG. 2. Connecting terminals 8, 11*a*, and 11*b* for cables are provided in the openings 5*c* and 5*d*. Each connecting terminal has a closable cover 9 as shown in FIG. 2. The X-ray image detector 10 is used as a cassette solely or combined with various kinds of support portions.

FIG. 3 is a perspective view showing an arrangement example which uses the X-ray image detector 10 combined with a radiographic imaging table 20.

In the radiographic imaging table 20, a top plate 21 on which an object is placed is supported to be movable in the horizontal plane. The top plate 21 is provided on a radiographic imaging table main body 22 via support portions 23. A storage unit 24 to attach the X-ray image detector 10 is provided between the top plate 21 and the radiographic imaging table main body 22. The storage unit 24 has, on its front surface, an opening portion 25 to insert the X-ray image detector 10. An X-ray tube 31 for emitting X-rays is arranged above the radiographic imaging table 20 to be movable along a guide portion 32.

To install the X-ray image detector 10 in the radiographic imaging table 20, the X-ray image detector 10 is attached in the storage unit 24, as indicated by an arrow A, or mounted on the top plate 21, as indicated by an arrow B.

In the method of attaching the X-ray image detector 10 in the storage unit 24, as indicated by the arrow A, the X-ray image detector 10 does not directly contact the object. This facilitates alignment between the object and the X-ray image detector 10. The method of mounting the X-ray image detector 10 on the top plate 21, as indicated by the arrow B, ensures degrees of freedom in locating the X-ray image detector 10 at various postures.

When using the X-ray image detector 10 solely as a cassette on the top plate 21, as indicated by the arrow B, the cables need to have flexibility and pose no problem even under a human body from the viewpoint of operability in alignment. Conversely, these requirements are unnecessary when the X-ray image detector 10 is attached inside the radiographic imaging table 20, as indicated by the arrow A.

Heat generated by the X-ray image detector 10 results from heat generation in the analog system at the time of charge reading from the X-ray image detection panel 1 in shooting or heat generation during image processing in the digital processing system. Since shooting requires power higher than in a standby state, average power consumption changes depending on the shooting interval. The heat generation amount also largely changes depending on the frame rate for shooting.

When portably using the X-ray image detector 10 solely, heat dissipation from the X-ray image detector 10 is determined by the heat dissipation performance from the surface of the exterior 5. Heat dissipation by natural convection generated by surface treatments or a radiating surface has a limit. Taking this into consideration, a frame rate Fo allowable in terms of heat dissipation performance is determined in advance. Note that the frame rate Fo is set to be lower than that when stationarily using the X-ray image detector 10 attached in the storage unit 24. Under these circumstances, extremely fast communication is unnecessary when portably using the X-ray image detector 10. Communication using metal-based cables can achieve sufficient performance. It is more important to implement a cable configuration without any trouble in operations by taking advantage of the flexibility of the metal cables. When a human body is placed on the X-ray image detector 10, unevenness in the direction of thickness readily causes uncomfortable bodily sensations. The X-ray image detector 10 is preferably as flat as possible. Hence, the cables preferably are led from a side surface. When portably using the X-ray image detector 10, a cable 6 is connected to the connecting terminal 8 provided on the side surface.

On the other hand, in the method of attaching the X-ray image detector 10 in the storage unit 24, as indicated by the arrow A, another cooling unit can be arranged, unlike when portably using the X-ray image detector 10. For example, the heat dissipation unit may include a fan and a vent (neither are shown) which are formed on a side surface of the storage unit 24 to cool the space formed by the X-ray image detector 10 and the storage unit 24 by an airflow. Such a heat dissipation system dissipates heat generated in the X-ray image detector 10 using an air layer of forcible convection on the back surface side of the case 5. Ventilation to the outside occurs via the vent formed in the storage unit 24. Hence, the frame rate for shooting can be set to be higher than that in portably using the X-ray image detector 10. Stable continuous shooting at a high frame rate is also possible. Since the X-ray image detector 10 is incorporated in the apparatus, the requirement of flexibility of the cables is less strict than that in the portably used X-ray image detector 10. For this reason, employing high-speed communication using, as an example, an optical communication cable makes it possible to raise the frame rate.

The X-ray image detector 10 has a unit for detecting the connecting terminal to which it is connected (to be described later in detail). Based on the connection state, the X-ray image detector 10 changes setting of the frame rate for shooting. The outer shape of the connecting terminal changes depending on, as an example, whether the X-ray image detector 10 is used solely or attached to a frame, considering not to connect a cable of wrong specifications. Accordingly, the communication unit and communication protocol for the control unit 82 and the shooting driving method of the X-ray image detection panel 1 are also switched. For example, if a cable is connected to the connecting terminal for single use to solely portably use the X-ray image detector 10, the X-ray image detector 10 is set in a still image shooting mode. Note that in the still image shooting mode, shooting is performed once for one irradiation input. To continuously shoot images, a moving image shooting mode is set. As the communication protocol, for example, versatile Ethernet® is used. A driving method of performing is used that charge accumulation for about 1 sec at maximum except in a special case and read for about 1 sec twice for shot image acquisition and correction image acquisition. Generally, since one object changes its posture, or the object itself changes, shooting is done at an interval of at least several ten sec and does not continue long.

To the contrary, when a cable 12 is connected to the connecting terminals 11a and 11b to attach the X-ray image detector 10 to the frame, the moving image shooting mode is set. Moving image shooting requires frame-by-frame shooting at 30 fps and may sometimes continue for several min. For this reason, the heat generation amount greatly increases as compared to the still image shooting mode. However, the cooling unit in the frame can cool the apparatus. Since the communication cable does not need high flexibility concerning operability, the connector may be divided as indicated by reference numeral 12 in FIG. 3 to partially employ an optical cable connected via an connector 12b. As indicated by a connector 12a, the cable can cope with an increase in the number of lines, unlike the cable in the still image system. This implements communication specifications with a speed higher than in the still image shooting mode.

Figure 5:
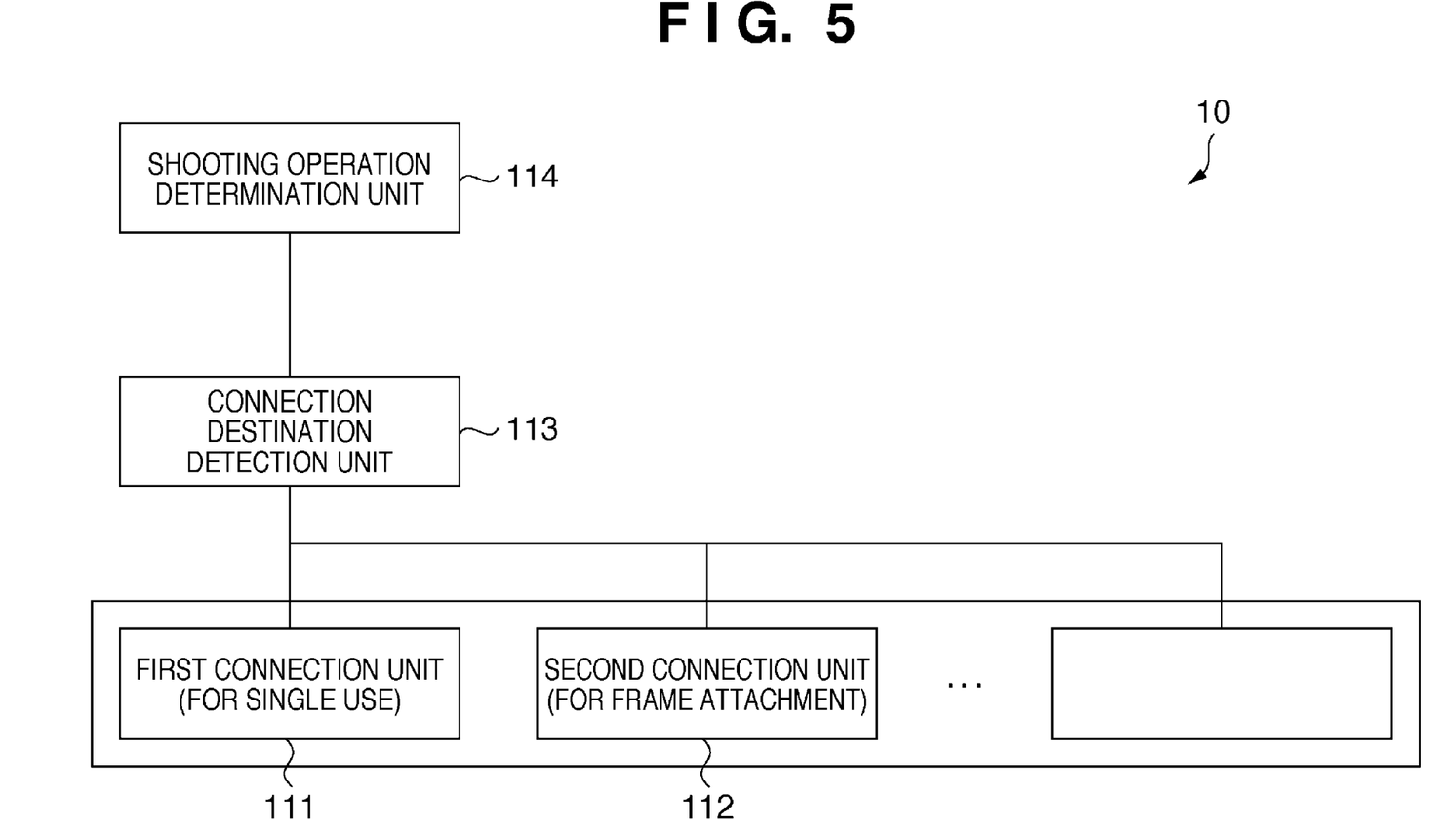
FIG. 5 is a block diagram showing an example of the functional arrangement of the X-ray image detector 10 shown in FIG. 1.

An example of the functional arrangement of the X-ray image detector 10 shown in FIG. 1 will be described herewith reference to FIG. 5.

The X-ray image detector 10 includes a first connection unit 111, a second connection unit 112, a connection destination detection unit 113, and a shooting operation determination unit 114.

The connecting terminal 8 for single use implements the first connection unit 111. The connecting terminals 11a and 11b for frame attachment implement the second connection unit 112. The first connection unit 111 and the second connection unit 112 serve as interfaces for power supply and signal transfer. Note that each connection unit may include a plurality of connecting terminals (e.g., a connecting terminal for power supply and that for signal transfer).

The connection destination detection unit 113 detects a connecting terminal to which a cable is connected. More specifically, the connection destination detection unit 113 detects the first connection unit 111 or the second connection unit 112 to which a cable is connected.

The shooting operation determination unit 114 determines the shooting operation of the X-ray image detector 10 based on the detection result from the connection destination detection unit 113. More specifically, when a cable is connected to the first connection unit 111, the shooting mode for still images is set (still image shooting mode). When a cable is connected to the second connection unit 112, the shooting mode for moving images is set (moving image shooting mode). That is, the frame rate for shooting is changed based on the connection state. The shooting operation determination unit 114 also switches the shooting driving method of the X-ray image detection panel 1 based on the communication specifications (e.g., transmission rate) of the connecting terminal connected to a cable. Note that switching the shooting driving method of the X-ray image detection panel 1 indicates switching between performing driving only once and performing driving twice for shot image acquisition and correction image acquisition.

Figure 6:
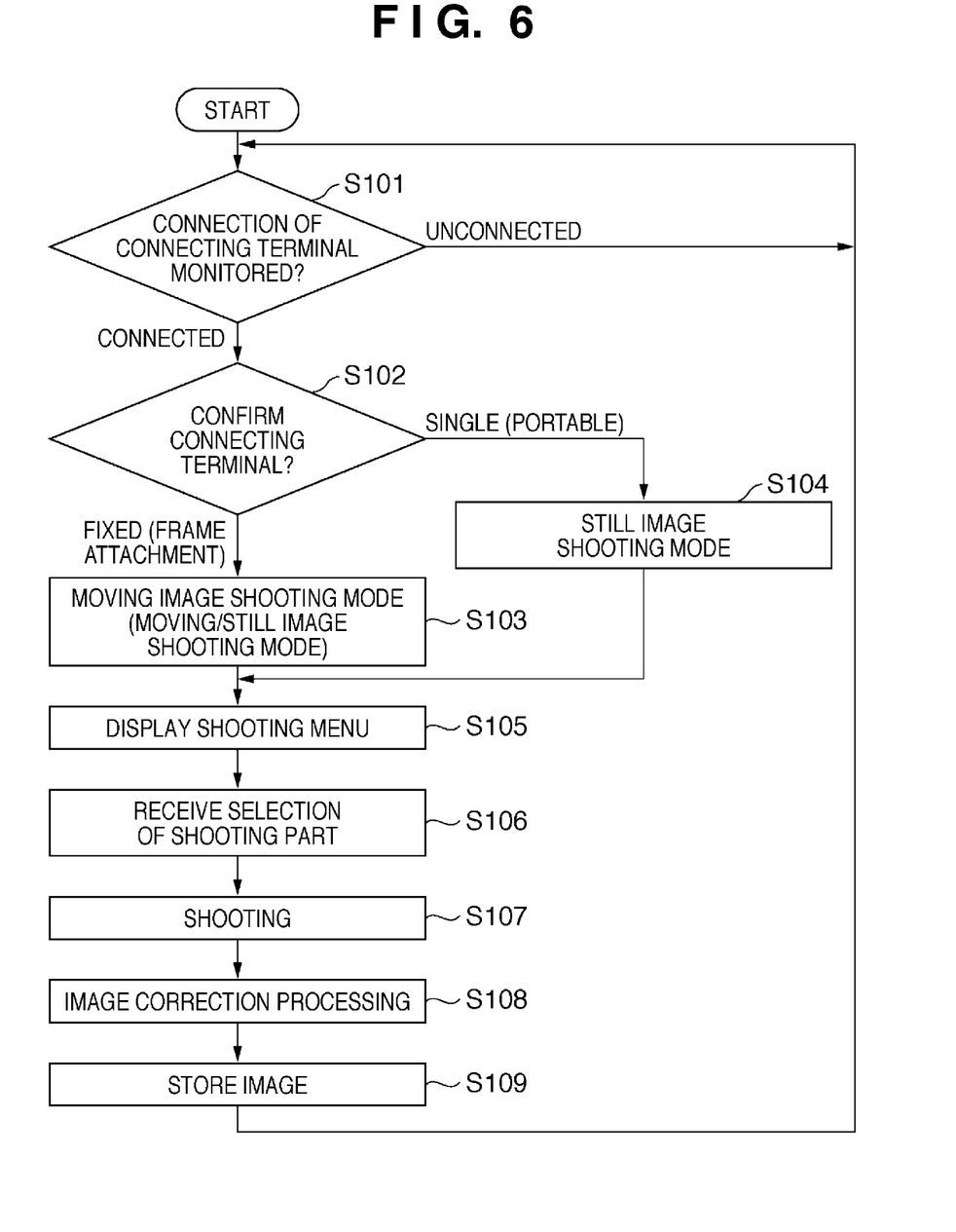
FIG. 6 is a flowchart illustrating an example of the operation of an X-ray imaging apparatus 80 shown in FIG. 1.

An example of the operation of the X-ray imaging apparatus 80 shown in FIG. 1 will be described next with reference to FIG. 6. Shooting of an X-ray image will be explained here.

When processing starts, the X-ray imaging apparatus 80 causes the connection destination detection unit 113 of the X-ray image detector 10 to detect the connecting terminal to which a cable is connected. If no cable is connected ("unconnected" in step S101), the connection destination detection unit 113 continues connection monitor. Upon detecting connection, the X-ray imaging apparatus 80 causes the shooting operation determination unit 114 of the X-ray image detector 10 to determine the X-ray imaging operation. As described above, the shooting operation to be determined includes the shooting mode permitted for the connecting terminal and the shooting driving method of the X-ray image detection panel 1. Shooting mode switching will be exemplified here.

If the connection destination detection unit 113 detects that a cable is connected to the first connection unit 111 ("single use" in step S102), the display unit 83 displays a shooting menu window that allows selection of the still image shooting mode (steps S104 and S105). On the other hand, if the connection destination detection unit 113 detects that a cable is connected to the second connection unit 112 ("fixed" in step S102), the display unit 83 displays a shooting menu window that allows selection of the moving image shooting mode (steps S103 and S105). Note that when a cable is connected to the second connection unit 112, not only the moving image shooting mode but also the still image shooting mode may be made selectable. For example, when a cable is connected to the first connection unit 111, the shooting menu window allows to select only the still image shooting mode. The moving image shooting mode is unselectable. However, when a cable is connected to the second connection unit 112, operation menus for both still images and moving images are selectable.

When the shooting menu window is displayed, the operator selects the shooting mode and shooting part (body part) via the input unit (not shown). When they are input, the X-ray imaging apparatus 80 receives the input operation (step S106) and executes shooting in the shooting mode determined by the above-described processing (step S107). After that, the X-ray imaging apparatus 80 performs image correction processing of the shot X-ray image (step S108) and stores the image in the storage unit (not shown) (step S109).

As described above, according to the first embodiment, it is possible to realize both convenience when using the X-ray image detector 10 solely (portably) and high performance when using the detector attached to a frame (fixed on a support portion). This makes it possible to provide an apparatus usable in various modes to shoot a moving image or a cassette still image.

Second Embodiment

The second embodiment will be described next. In the second embodiment, an example will be explained in which an X-ray image detector 10 is combined with a mobile C arm unit. The functional arrangements of an X-ray imaging apparatus 80 and the X-ray image detector 10 according to the second embodiment are the same as in FIGS. 1 and 5 described in the first embodiment, and a detailed description thereof will not be repeated.

Figure 7:
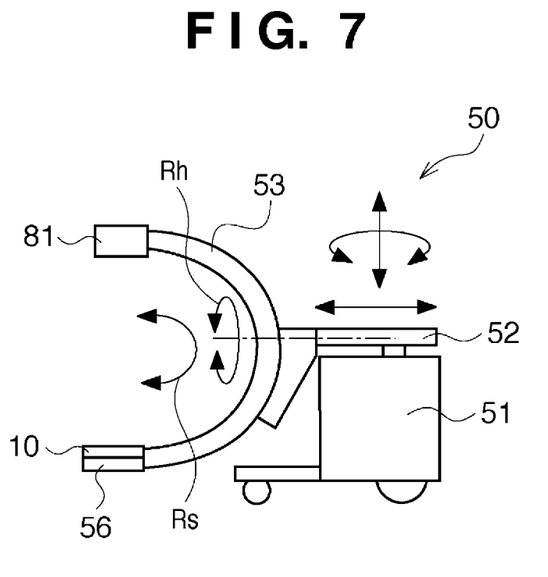
FIG. 7 is a view showing an example in which an X-ray image detector 10 according to the second embodiment is attached to a C arm.
Figure 8:
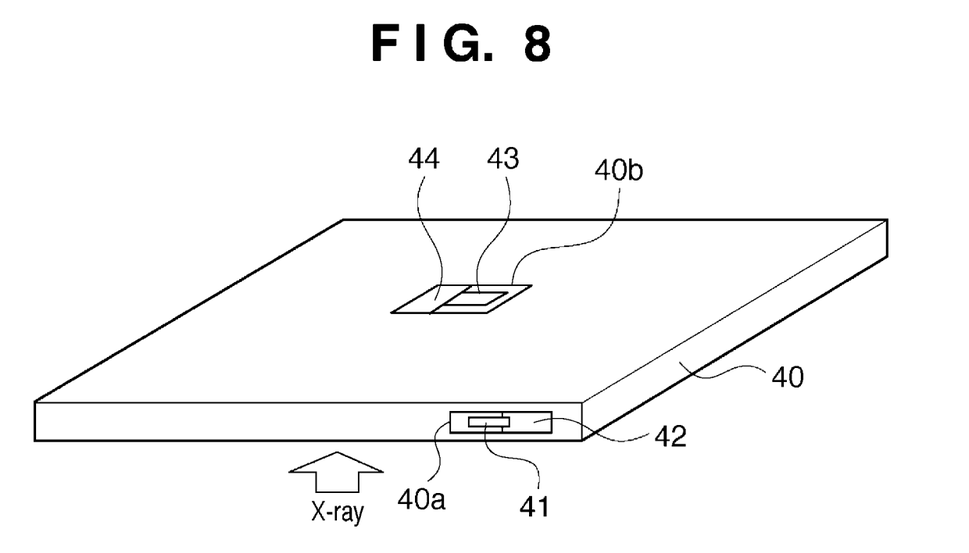
FIG. 8 is a perspective view showing an example of the outer appearance of the X-ray image detector 10 according to the second embodiment.
Figure 9:
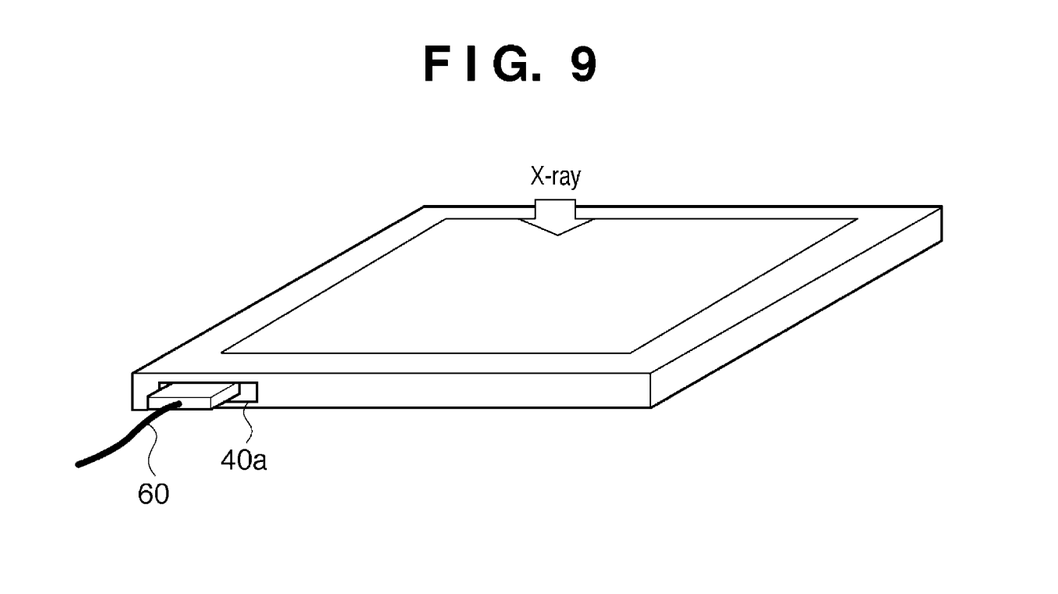
FIG. 9 is a perspective view showing an example of the connection state of the X-ray image detector 10 according to the second embodiment when portably used.
Figure 10:
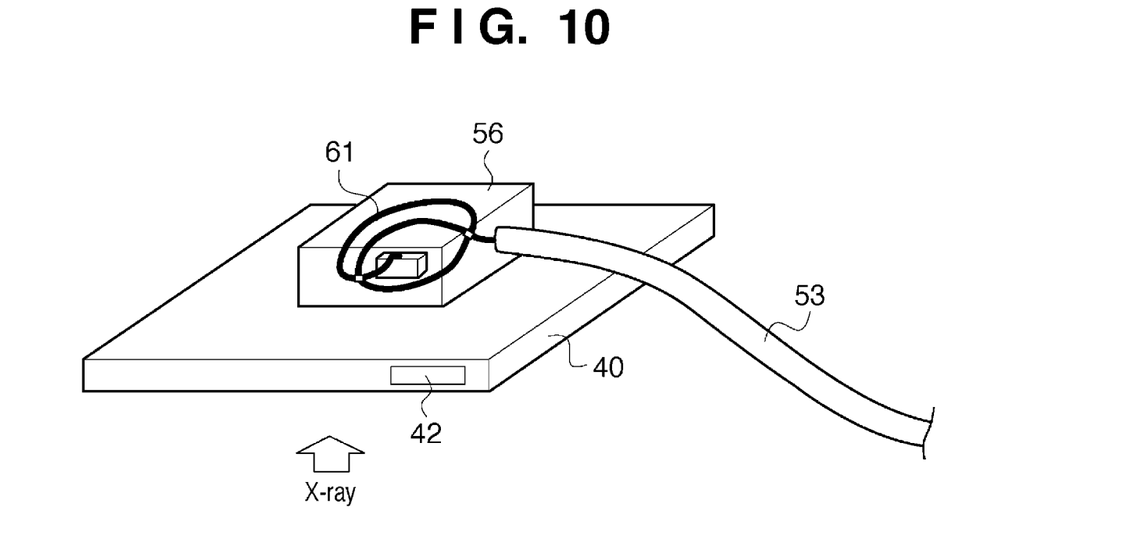
FIG. 10 is a perspective view showing an example of the connection state of the X-ray image detector 10 according to the second embodiment when attached to the C arm.

The X-ray image detector 10 according to the second embodiment will be described with reference to FIGS. 7 to 10. FIG. 7 is a view showing an example in which the X-ray image detector 10 is attached to a C arm. FIG. 8 is a perspective view showing an example of the outer appearance of the X-ray image detector 10. FIG. 9 is a perspective view showing an example of the connection state of the X-ray image detector 10 when portably used. FIG. 10 is a perspective view showing an example of the connection state of the X-ray image detector 10 when attached to the C arm.

Referring to FIG. 7, a mobile C arm unit 50 includes a horizontal shaft 52 supported by a main body 51, and an arm member 53 having a C shape and provided at the distal end of the horizontal shaft 52. These units can rotate and move as indicated by the arrows in FIG. 7. The C arm member 53 has, at its two ends, an X-ray generator 81 and the X-ray image detector 10, which face each other and are used while being positioned at an arbitrary posture by the above-described mechanism.

A holder unit 56 provided at the distal end of the C arm detachably holds the X-ray image detector 10. The X-ray image detector 10 is also supported to make rotation Rs about the X-ray incident axis. In this case, the X-ray image detector 10 has a rectangular shape. For this reason, the shooting area determined by positioning to a human body also changes, unlike a conventional image intensifier having a cylindrical shape. Rotating the X-ray image detector 10 allows positioning to a desired shooting area. At this time, a cable led to a side surface of the X-ray image detector 10 not only impedes positioning to a human body but also makes troubles concerning operability so that, for example, someone may trip over the cable.

In the second embodiment, focus is placed on the above-described point. As shown in FIG. 8, cable connecting terminals 41 and 43 are arranged at two points, that is, in an opening portion 40a formed in the back surface facing the X-ray incident surface and in an opening portion 40b formed in a side surface perpendicular to the X-ray incident surface. Closable covers 42 and 44 cover the connecting terminals 41 and 43, respectively. Springs (not shown) bias the covers 42 and 44 in a closing direction.

When portably using the X-ray image detector 10, the connecting terminal 41 on the side surface is used, as shown in FIG. 9, like the first embodiment. When using the X-ray image detector 10 attached to the C arm, the connecting terminal 43 on the back surface is used, as shown in FIG. 10. When the X-ray image detector 10 is attached to the C arm, a connection destination detection unit 113 detects the attachment. An electromagnetic lock unit in the X-ray image detector locks the cover on the side surface and unlocks the cover on the back surface. To the contrary, when the X-ray image detector 10 is not attached to the C arm, the electromagnetic lock unit unlocks the cover on the side surface and locks the cover on the back surface. Such an interlock mechanism prevents any error to connect a cable to a wrong portion.

The X-ray image detector 10 is connected to the C arm. A cable 61 is connected to the connecting terminal 43 on the back surface. The cable 61 is wound and stored at almost the center of the X-ray image detector not to make any trouble even during rotation of the X-ray image detector 10.

The second embodiment has been described above. The operation of the X-ray imaging apparatus 80 according to the second embodiment is the same as in FIG. 6 described above in the first embodiment, and a description thereof will not be repeated.

Typical embodiments of the present invention have been described above. However, the present invention is not limited to the aforementioned and illustrated embodiments, and can be properly modified without departing from the scope of the invention.

Figure 11:
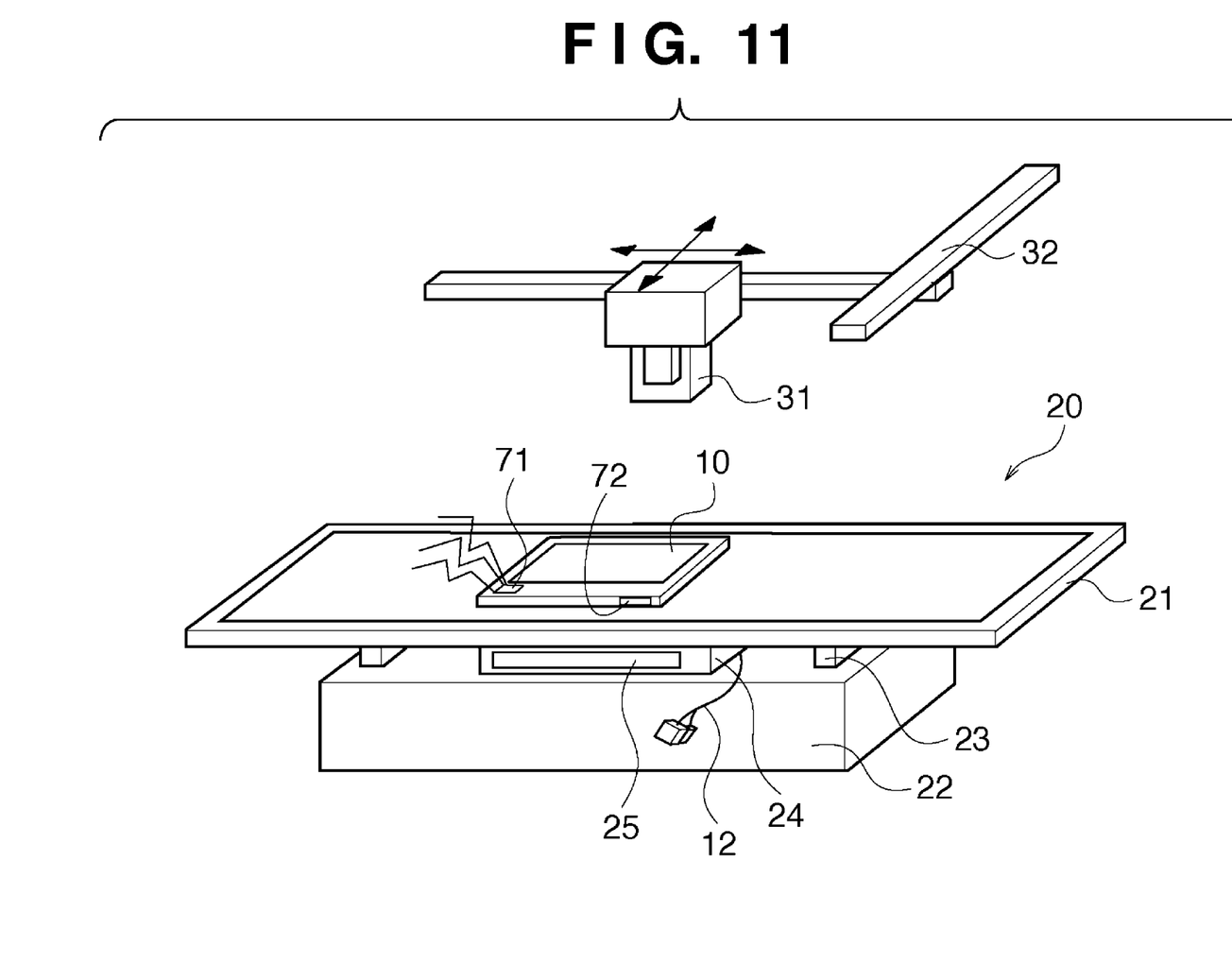
FIG. 11 is a perspective view showing an example of a modification.

For example, the X-ray image detector 10 may have a wireless communication function. This will be described briefly with reference to FIG. 11. FIG. 11 shows an arrangement example which combines a radiographic imaging table 20 as in the above-described first embodiment and the X-ray image detector 10 having wireless communication function. The X-ray image detector 10 includes both a connection unit 71 which performs wireless communication and a connection unit 72 which performs wired communication. The X-ray image detector 10 is attached in a storage unit 24. When a cable 12 is connected to the connecting terminal 72 of the X-ray image detector 10, shooting at a high frame rate in a moving image shooting mode is permitted, as in the first embodiment. On the other hand, when portably using the X-ray image detector 10 on a top plate 21, the X-ray imaging apparatus 80 first establishes wireless communication with the X-ray image detector 10. When the X-ray imaging apparatus 80 recognizes the X-ray image detector 10, they start wireless communication. At this time, only a still image shooting mode is permitted. The succeeding operation is the same as in the first embodiment, and a description thereof will not be repeated.

The support portion to be combined with the X-ray image detector 10 is not limited to the above-described radiographic imaging table 20. For example, an upright stand or a universal stand is also usable.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

According to the present invention, it is possible to realize both convenience when portably using a detector and high performance when stationarily using the detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-220500, filed on Aug. 28, 2008, which is hereby incorporated by reference herein in its entirety.

What is claimed is:

1. A radiographic imaging apparatus comprising:
a radiation generator configured to irradiate an object with radiation;
a detection unit configured to detect the radiation generated by the radiation generator and transmitted through the object, thereby shooting a radiographic image; and
a control unit configured to control radiographic imaging by the radiation generator and the detection unit,
the detection unit comprising:
a first connection unit configured to be used to connect the control unit when used portably;
a second connection unit configured to be used to connect the control unit when stationarily used on a support portion;
a connection destination detection unit configured to detect which one of the first connection unit and the second connection unit is used to connect the control unit; and
a determination unit configured to determine a shooting operation based on a detection result of the connection destination detection unit,
wherein upon detecting connection by the first connection unit, the determination unit makes a frame rate of shooting lower than that in connection by the second connection unit.

2. The apparatus according to claim 1, wherein
the first connection unit is provided on a side surface of the detection unit perpendicular to an incident plane of the radiation, and
the second connection unit is provided on a bask surface of the detection unit facing the incident plane of the radiation.

3. The apparatus according to claim 1, wherein the first connection unit and the second connection unit are used for communication with the control unit and use different communication protocols.

4. The apparatus according to claim 1, wherein the first connection unit and the second connection unit include connecting terminals which are used for connection and have different shapes.

5. The apparatus according to claim 1, wherein the determination unit determines a shooting driving method of the detection unit based on communication specifications of a connection unit whose connection is detected by the connection destination detection unit.

6. The apparatus according to claim 1, wherein
the first connection unit is used for wireless communication with the control unit, and
the second connection unit is used for wired communication with the control unit.

7. A control method of a radiographic imaging apparatus including:
a radiation generator configured to irradiate an object with radiation;
a detection unit configured to detect the radiation generated by the radiation generator and transmitted through the object, thereby shooting a radiographic image; and
a control unit configured to control radiographic imaging by the radiation generator and the detection unit, the method comprising:
detecting which one of a first connection unit provided in the detection unit and used to connect the control unit when portably using the detection unit and a second connection unit provided in the detection unit and used to connect the control unit when stationarily using the detection unit on a support portion is used to connect the detection unit to the control unit; and
determining a shooting operation based on a detection result in the detecting which one of the first connection unit and the second connection unit is used to connect the detection unit to the control unit,
wherein upon detecting connection by the first connection unit, a frame rate of shooting is made lower than that in connection by the second connection unit in the determining of the shooting operation.

* * * * *